(12) United States Patent
Wang et al.

(10) Patent No.: US 7,662,607 B2
(45) Date of Patent: Feb. 16, 2010

(54) CHALAROPSIS LYSOZYME PROTEIN AND ITS METHOD OF USE IN ANTI-BACTERIAL APPLICATIONS

(75) Inventors: Zhongmin Wang, Madison, AL (US); Daniel C. Carter, Huntsville, AL (US)

(73) Assignee: New Century Pharmaceuticals, Inc., Huntsville, AL (US)

( * ) Notice: Subject to any disclaimer, the term of this patent is extended or adjusted under 35 U.S.C. 154(b) by 185 days.

(21) Appl. No.: 10/566,243

(22) PCT Filed: Jul. 30, 2004

(86) PCT No.: PCT/US2004/024414

§ 371 (c)(1),
(2), (4) Date: Jul. 31, 2006

(87) PCT Pub. No.: WO2005/011587

PCT Pub. Date: Feb. 10, 2005

(65) Prior Publication Data

US 2007/0253945 A1    Nov. 1, 2007

Related U.S. Application Data

(60) Provisional application No. 60/490,984, filed on Jul. 30, 2003.

(51) Int. Cl.
*C12N 9/36* (2006.01)
*C12P 21/06* (2006.01)
*C07H 21/02* (2006.01)
*C07H 21/04* (2006.01)

(52) U.S. Cl. ............. 435/206; 435/69.1; 536/23.1; 536/23.2

(58) Field of Classification Search .......... None
See application file for complete search history.

(56) References Cited

U.S. PATENT DOCUMENTS 5,326,858 A    7/1994   Lichenstein et al.
5,514,572 A *  5/1996   Veronese et al. ............ 435/180
6,583,272 B1 * 6/2003   Bailon ........................ 530/397

OTHER PUBLICATIONS

Fouche et al., The N,O-Diacetylmuramidase of *Chalaropsis* species. J. Biol. Chem., 1978, vol. 253 (19): 6787-6793.*
Hash et al, "The N, O-Diacetylmuramidase of *Chalaropsis* species. I. Purification and Crystallization" 1967, pp. 5586-5590, vol. 242, No. 23, Journal of Biological Chemistry.
Mitchell et al, "The N, O-Diacetylmuramidase of *Chalaropsis* species. II. Physical properties" 1999, pp. 17-21, vol. 244, No. 1, Journal of Biological Chemistry.
Shih et al, "The N, O-Diacetylmuramidase of *Chalaropsis* species. III. Amino acid composition and partial structural formula." 1971, pp. 994-1006, vol. 246, No. 4, Journal of Biological Chemistry.
Wahba et al, "The N, O-Diacetylmuramidase of *Chalaropsis* species. IV. Tryptic peptides." 1975, pp. 3709-3712, vol. 20, No. 10, Journal of Biological Chemistry.
Felch et al, "The N, O-Diacetylmuramidase of *Chalaropsis* species. V. The complete amino acid sequence", 1975, pp. 3713-3720, vol. 250, No. 10, Journal of Biological Chemistry.
Shimonishi et al, "Cloning and expression of the N-acetylmuraidase gene from *Strerptomyces rutgersensis* H-46" 1999, pp. 362-367, vol. 88, No. 4, Journal of Bioscience and Bioengineering.

* cited by examiner

*Primary Examiner*—Ganapathirama Raghu
(74) *Attorney, Agent, or Firm*—B. Aaron Schulman; Stites & Harbison PLLC (57) ABSTRACT

A Chalaropsis lysozyme (Lysozyme Ch) is provided which has a corrected amino acid sequence and which can be utilized to prepare recombinant proteins having higher activity than those proteins using the incorrect sequence. Methods are also provided to reduce immunogenicity or increase half-life of the lysozyme. The lysozyme Ch of the present invention will be extremely useful in killing bacteria, particularly resistance strains such as MRSA and VISA, and the enzyme can be utilized in a variety of settings wherein bacterial infection has been a particular problem such as the hospital setting or in veterinary applications, and can also be used as an effective means of combating bioterror agents.

2 Claims, 7 Drawing Sheets

+ CHITOSAN OLIGO

+ GLUCOSAMINE

NO INHIBITOR

LYSOZYME CH

HEW LYSOZYME

+ NAG$_3$

+ NAG

NO INHIBITOR

```
1                        
TVQGFDISSY  QPSVNFAGAY  SAGARFVIIK  ATEGTSYTNP  40
          -           -           -           -
          -           -           -           -
41                       
SFSSQYNGAT  TATGNYFIRG  GYHFAHPGET  TGAAQADYFI  80
          N-G         -           -           -
     -T-    -           -           -
81                       
AHGGGWSGDG  ITLPGMLDLE  SEGSNPACWG  LSAAASMVAWI  120
          -           -           -           -
          -           -           -           -
121                      
KAFSDRYHAV  TGRYPMLYTN  PSWWSSCTGN  SNAFVNTNPL  160
          -           -           -           -
          -           -           -           -
161                      
VLANRYASAP  GTIPGGWPYQ  TIWQNSDAYA  YGGSNNFING  200
          -           -           -           -
          -           -           -           -
201                      
SIDNLKKLAT  G
   -A-      -
```

*FIG. 8*

CHALAROPSIS LYSOZYME PROTEIN AND ITS METHOD OF USE IN ANTI-BACTERIAL APPLICATIONS

CROSS-REFERENCE TO RELATED APPLICATIONS

The present application claims the benefit of U.S. provisional application Ser. No. 60/490,984, filed Jul. 30, 2003, incorporated herein by reference.

FIELD OF THE INVENTION

The present invention relates in general to a lysozyme produced from a *Chalaropsis* species of fungi, and in particular to a *Chalaropsis* lysozyme having a corrected amino acid sequence so as to allow recombinant production of this enzyme with a higher activity, as well as to the atomic coordinates thereof, and the use of this lysozyme as an antibacterial agent in applications wherein killing of bacteria, particularly highly resistant bacteria such as methicillin-resistant or vancomycin-intermediate staphylococci, is desired.

BACKGROUND OF THE INVENTION

For many years, antibiotics have been used to combat bacterial infection, most commonly in the hospital setting, and have thus become an integral part of our lives. Since the discovery of penicillin by Dr. Alexander Fleming in 1928, many generations of β-lactam antibiotics which target the cell wall synthesis pathway have been introduced. However, since the introduction of β-lactam antibiotics, over the years bacteria have developed significant resistance. The earliest resistance of *S. aureus* and other bacteria comes from a family of proteins called penicillinases, which have the capability of binding penicillins, hydrolyzing the β-lactam ring, thus rendering the inactivity of the antibiotics.

One such bacteria, *Staphylococcus aureus*, commonly found in hospital settings on the skin and inside the noses of humans and animals, has quickly evolved into a "super-bug". Previously, methicillin, a semi-synthetic penicillin derivative, was designed to have a rigid β-lactam ring and to disrupt the cell wall synthesis pathway of these bacteria. However, resistance from *S. aureus* began to appear just one year after Methicillin's introduction, and Methicillin-resistant *S. aureus* (MRSA) have quickly spread to hospitals worldwide where there is an alarmingly high prevalence of these bacteria. It is thought that this bacterial resistance arises from the acquisition of the mecA gene via horizontal transfer from an unidentified species. The mecA gene encodes a new penicillin-binding protein (PBP2a), which has unusually low β-lactam affinity and remains active to allow cell wall synthesis even at normally lethal antibiotics concentrations. As MRSAs are resistant to other classes of antibiotics, glycopeptides such as vancomycin emerged as the possible last defense against MRSA infections. Unfortunately, but not surprisingly, scientists and clinicians have now recognized the appearance of a vancomycin-resistant MRSA strain (also referred to as Vancomycin-intermediate *S. aureus* or VISA), first in Japan in 1996, and subsequently in the United States, France, Korea, South Africa and Scotland, and this further emphasizes the urgent need for new and more effective antibiotics which would be harder for bacteria to overcome and develop resistance against The problems presented by bacteria and other pathogenic agents have become more dangerous since Sep. 11, 2001 and the anthrax scare in the fall of 2001, and bioterrorism has become a serious concern of our nation and the world. In fact, *S. aureus* was identified by CDC as a level 2 bioterrorism threat, due to the lethal toxicity from the *Staphylococcal Enterotoxin* B. Bacteria such as *S. aureus* also affect other industries such as milk production in that the inflammatory infection of *S. aureus* in cows' mammary glands, Mastitis, causes them to produce poor-quality milk that can not be made into cheese, butter or yogurt. This costs the dairy industry an estimated $1.7 billion in the United States alone.

One avenue for fighting and treating bacterial infection that has been studied over the years has been the use of lysozymes. Lysozymes are enzymes which attack bacteria by cleaving their oligosaccharide backbone of the cell walls, a mechanism different from the β-lactams, and many bacteria have been observed to have difficulties developing resistance for it. One particular type of enzyme, the Lysozyme from fungi of the species *Chalaropsis*, which is known as *Chalaropsis* lysozyme, or Lysozyme Ch, and which is a N,O-diacetylmuramidase, has the ability to kill *S. aureus* and has previously been thought of as a good agent to be used in antibacterial agents. It can also be developed as an early detection method of *staphylococcal* contaminations or infections, and this family of Lysozymes has been shown to significantly reduce the total number of both Gram-positive and Gram-negative bacteria when applied in meat products, including *Clostricium Botulinum*, identified by CDC as the number two bioterrorism threat, second to smallpox. It is thought that the action of Lysozymes cleave the oligosaccharide backbone of the bacterial cell wall, resulting a weakened cell wall and eventual cell lysis and death. Lysozyme Ch, produced extracellularly by the fungus *Chalaropsis* species, is unusual among Lysozymes by having both β-1,4-N-acetylmuramidase and β-1,4-N,6-O-diacetylmuramidase activities. The later activity accounts for its ability to kill *S. aureus* whose cell walls contain 6-O acetylated peptidoglycans such as N,6-O-diacetylmuramic acid, and recent studies with an enzyme of bacteriophage γ, PlyG, being highly effective for killing *B. anthracis*, demonstrate the achievability of anti-bacterial Lysozymes. Moreover, the bacteria did not develop a resistance even after being treated with chemicals which normally increase the percentage of mutants resistant to standard antibiotics.

The present inventors have now determined that although the sequence of Lysozyme was published, this actual sequence is wrong. Accordingly, if one tried to generate recombinant lysozyme using the previously published sequence, it would not have the activity of the correct sequence. It is thus a highly desirable object to obtain the correct sequence of Lysozyme Ch so as to be able to use this protein as a solution to the ever growing problem of bacterial infections such as MRSA and VISA. It thus remains a highly desirable object to be able to provide a Lysozyme Ch of maximal antibacterial activity so as to develop more effective methods of treating and preventing the spread of bacteria which will be of great importance in hospitals, veterinary medicine, and in the fight against bioterrorism.

SUMMARY OF THE INVENTION

Accordingly, it is an object of the present invention to provide improved versions of lysozyme Ch which can be more effective in killing bacteria so as to treat and prevent the spread of harmful bacteria such as resistant strains of *S. aureus*.

It is also an object of the present invention to provide isolated enzymes having a specific amino acid sequence which are useful in methods to treat, prevent or diagnose bacterial infections.

It is another object of the present invention to provide pharmaceutical compositions including the improved form of lysozyme Ch along with pharmaceutically acceptable vehicles, carriers or excipients which can be used to treat and protect against infections from bacteria and other pathogens.

It is yet another object of the present invention to provide nucleic acids which code for the improved proteins of the present invention and for antibodies which recognize the amino acid sequence of the present invention.

It is further an object of the present invention to provide the atomic coordinates for the proteins of the present invention.

It is still further an object of the invention to provide methods for making the proteins of the invention less immunogenic and/or with a greater half-life, and methods for utilizing the proteins of the invention to treat or prevent bacterial infection in the hospital setting, in veterinary applications, and in preparations designed to deal with bioterror agents such as Anthrax and other pathogens.

These and other objects are provided by virtue of the present invention which arises from the discovery of the present inventors that the previous sequences proposed for Lysozyme Ch were incorrect, and that by preparing recombinant proteins having the corrected sequence as set forth herein, an improved and more active Lysozyme Ch is obtained which will have higher antibacterial activity than recombinant proteins which are prepared using the incorrect sequence. In addition, the present inventors have at least identified three specific pairs of amino acid residues in Lysozyme, namely Asp 6 and Asp 194, Glu 33 and Glu 102, and Asp 98 and Glu 100, which are highly important to the ability of lysozyme Ch to disrupt the bacterial cell wall and thus be highly effective in killing bacteria. The lysozyme proteins of the present invention can also be made less immunogenic or with improved half-life through various means including PEGylation, glycosylation or "hyperglycosylation", and the activity is further enhanced by complexing the lysozyme Ch with an agent such as glucosamine prior to attachment to the immunogenicity-reducing agent. These agents further have been shown to result in a lysozyme Ch with increased activity and effective half-life thus even further improving its effectiveness in killing bacteria and treating or preventing infections. Nucleic acids encoding the corrected version of Lysozyme Ch are also contemplated in the present invention, and such nucleic acids will be utilized in recombinant means for preparing the lysozyme Ch of the present invention. In addition, antibodies which recognize the sequence of the present protein will be more useful in determining the presence of lysozyme Ch and will thus be useful in identifying infections, such as in a diagnostic kit which is used in determining whether such lysozymes are present. Finally, the invention provides the atomic coordinates of lysozyme Ch which will be further useful in eliciting information concerning this protein and in methods of obtaining and using lysozyme Ch.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

The descriptions of the drawing figures are included below.

DETAILED DESCRIPTION OF THE PREFERRED EMBODIMENTS

In accordance with the present invention, the present inventors have now discovered that the commonly accepted amino acid sequence for Lysozyme Ch is in error, and that the actual sequence, when isolated and produced recombinantly, will have a higher activity level and will thus be far more effective in killing bacteria that recombinant proteins produced using the incorrect original sequence. The Lysozyme enzymes from the fungus of the *Chalaropsis* species have been the subject of numerous articles in the field, including Hash, *J. Bacteriol.* 93(3):1201-1202 (1967); Hash et al., *J. Biol Chem.* 242(23): 5580-5590 (1967); Fouche et al., *J. Biol Chem.* 253(19): 6787-6793 (1978); and Lyne et al., *J. Biol Chem.* 265(12): 6928-6930 (1990). The original sequence for Lysozyme Ch, identified as the N,O-diacetylmuramidase for the *Chalaropsis* species, was published by Felch et al. at *J. Biol Chem.* 250(10):3713-3720 (1975). Still further information about the Lysozyme Ch structure was described in Rau et al., *J. Biol Chem.* 276(34)31994-31999 (2001). All of the foregoing articles are incorporated herein by reference.

Following the establishment of this sequence, there had been very little challenge to the accuracy of this sequence since there had been very little in the way of structural information that was available for this enzyme. However, the present inventors carried out high resolution studies of the atomic structure of Lysozyme Ch and the information in the form of atomic coordinates is provided herewith in Appendix A. Based on these high resolution studies. and the electron density data obtained therein, the present inventors have thus determined that the actual sequence for Lysozyme Ch differs in important ways than the sequence as disclosed in prior references and until now considered the accurate Lysozyme Ch sequence. The corrected sequence is shown below in comparison to the original incorrect sequence, and the changes from the original sequence are highlighted in bold text:

```
Original    TVQGFDISSY QPSVNFAGAY SAGARFVIIK    40
            ATEGTSYTNP
Corrected   TVQGFDISSY QPSVNFAGAY SAGARFVIIK
            ATEGTSYTNP
```

```
                                          -continued
Original      SFSSQYNGAT  TATGNYFIRG  GYHFAHPGET   80
              TGAAQADYFI
Corrected     SFSSQYTGAT  NAG___FIRG  GYHFAHPGET
              TGAAQADYFI Original      AHGGGWSGDG  ITLPGMLDLE  SEGSNPACWG  120
              LSAASMVAWI
Corrected     AHGGGWSGDG  ITLPGMLDLE  SEGSNPACWG
              LSAASMVAWI Original      KAFSDRYHAV  TGRYPMLYTN  PSWWSSCTGN  160
              SNAFVNTNPL
Corrected     KAFSDRYHAV  TGRYPMLYTN  PSWWSSCTGN
              SNAFVNTNPL Original      VLANRYASAP  GTIPGGWPYQ  TIWQNSDAYA  200
              YGGSNNFING
Corrected     VLA_RYASAP  GTIPGGWPYQ  TIWQNSDAYA
              YGGDSNIFNG Original      SIDNLKKLAT  G
Corrected     SADNLKKLAT  G
```

The corrected sequence is also identified herein as SEQ ID NO:1, and the original sequence is identified as SEQ ID NO:2. For purposes of uniformity and simplicity, the numbers of the amino acid positions from the original sequence have been used in the description below. In accordance with the invention, the protein having this sequence is deemed to include any derivatives of this sequence which maintain the same biological activity of the protein having the sequence of SEQ ID NO:1

In the corrected sequence of the present invention, the total number of amino acids has decreased from 211 to 207, and the sequence corrections occur at various places throughout the entire molecule. These changes include deletions of the three amino acids from 54 to 56, and changes to the amino acid residues at positions 47, 51 and 53. Interestingly, although the Asn 164 is generally conserved in the family, the electron density of Lysozyme Ch clearly showed the deletion of this residue. Next, the residues Phe 197 and Ile 198 are shown to be swapped.

The most important difference of all appears to be at position 194 which our data shows to be Asp and not Ser. Although Asp 6 has been implicated to be involved in the catalytic activity of the enzyme, due to the purported lack of an acidic or neutral hydrogen bonding partner, this role could not be confirmed definitively. However, in light of the information provided herein with the correction to the sequence, the change from Ser to Asp as position 194 puts an acidic amino acid right next to the Asp 6, and forms the basis of the functional mechanism. It is further the case that based on the new structure, there are at least three particularly active pairs of amino acid residues in the Lysozyme Ch molecule of the invention which appear to impart the N,O-diacetylmuramidase activity, and these three pairs of active amino acid residues including Asp 6 and Asp 194 (Asp 190 in the corrected protein); Glu 33 and Glu 102 (Glu 99 as corrected); and Asp 98 (Asp 95 corrected) and Glu 100 (Glu 97 corrected).

The new sequence thus has the amino acids as follows:

```
                                                 (SEQ ID NO:1)
     TVQGFDISSY  QPSVNFAGAY  SAGARFVIIK  ATEGTSYTNP

SFSSQYTGAT  NAGFIRGGYH  FAHPGETTGA  AQADYFIAHG

GGWSGDGITL  PGMLDLESEG  SNPACWGLSA  ASMVAWIKAF

SDRYHAVTGR  YPMLYTNPSW  WSSCTGNSNA  FVNTNPLVLA

RYASAPGTIP  GGWPYQTIWQ  NSDAYAYGGD  SNIFNGSADN

LKKLATG
```

This differs from the original sequence as set forth above, and the original sequence is as follows:

```
                                                 (SEQ ID NO:2)
     TVQGFDISSY  QPSVNFAGAY  SAGARFVIIK  ATEGTSYTNP

SFSSQYNGAT  TATGNYFIRG  GYHFAHPGET  TGAAQADYFI

AHGGGWSGDG  ITLPGMLDLE  SEGSNPACWG  LSAASMVAWI

KAFSDRYHAV  TGRYPMLYTN  PSWWSSCTGN  SNAFVNTNPL

VLANRYASAP  GTIPGGWPYQ  TIWQNSDAYA  YGGSNNFING

SIDNLKKLAT  G
```

Accordingly, the lysozyme Ch protein as set forth in SEQ ID NO:1 above will be useful when isolated and/or purified for use as an antibacterial agent, and recombinant proteins having these sequence will have a greater activity than proteins which can be constructed using the previously accepted sequence.

As will be set forth below, since this sequence will be useful in killing bacteria in a wide range of settings and applications, the invention also includes nucleic acids coding for this sequence, vectors containing the nucleic acids which can be used in recombinant methods of producing the novel *Chalaropsis* lysozyme of the present invention. In addition, the present invention contemplates the production and use of pharmaceutical compositions containing the isolated and/or purified enzyme of the present invention as described above, methods of utilizing the protein of the invention to kill bacteria, and recombinant methods of preparing the protein of the invention.

Further, to make the proteins of the invention more suitable for use with human or animal patients, it is preferred that the protein of the invention be made less immunogenic or half an increased half-life using any of a variety of methods by which mask the surface residues and optionally also have active sites inhibited so as to improve the effect of the masking agent. In this regard, there are several inhibitors of the active sites which can be used in order to reduce immunogenicity. In the preferred embodiment, the addition of a polyethylene glycol (PEG), also known as "PEGylation", can be used to reduce immunogenicity or increase half-life of the lysozyme Ch of the invention. The PEG can be any single chain or branched PEG's, and this compound can be coupled with the lysozyme-Ch of the invention in any suitable manner conventionally known to obtain such couplings.

In certain conditions, PEGylation has sometimes been shown to reduce immunogenicity for a number of enzymes and antibodies for injection into human body yet interfere with the enzymatic activities possibly due to attachment of PEG to active site groups. However, in the present invention, a PEGylated protein was observed to have greater activity than the native protein, and thus it is preferred that PEG groups be added which not only reduce immunogenicity but also increase the activity of the lysozyme-Ch. In one preferred embodiment, the lysozyme of the invention was complexed with methoxypolyethylene glycol succinimidyl succinate (MPSS), and this PEGylated lysozyme was shown to have increased activity over the native protein.

In addition, PEGylation can also be carried out in the presence of an active site or reversible inhibitor which is intended to block the access of PEG to the active site. Accordingly, it is preferred to complex the lysozyme with an active site inhibitor prior to the attachment of PEG. One such reversible inhibitor which can be used in the present invention are chitosan oligosaccharides. In addition, another method of reducing the immunogenicity of lysozyme-Ch is to complex the lysozyme using a glucosamine monomer or polymer as the active site inhibitor prior to the attachment to PEG. Any glucosamine which can block the active site is suitable for use in the invention, such as the glucosamine monomer or its polymers such as tetraglucosamine or heptaglucosamine.

Still another procedure to reduce immunogenicity is glycosylation or "hyperglycosylation". Hyperglycosylation is a well known procedure and is described, e.g., in Nakamura et al., *J Biol Chem.* 268(17):12706-12 (1993), said article incorporated herein by reference.

In accordance with the present invention, the invention contemplates the use of the lysozyme Ch of the present invention in methods of killing bacteria wherever such antibacterial activity is sought. This can be in a variety of settings, including hospital settings, both for patients and medical equipment or implants, food processing, around the home or office where antibacterial treatment is necessary, and in veterinary applications such as to treat or prevent Mastitis in dairy cows. In such cases, the method comprises applying the lysozyme Ch of the present invention to the particular situation in a form and amount effective to kill bacteria. By effective amount is meant that amount necessary to kill bacteria, and one skilled in the art would recognize that such an amount may differ depending on the nature and condition of the particular application. With regard to a human or animal patient, the effective amount would be that non-toxic amount of the lysozyme-Ch which would be administered to kill bacteria, and once again the effective amount would be based on the nature and condition of the patient.

In accordance with the invention, pharmaceutical compositions are provided which comprise the lysozyme Ch of the invention along with a pharmaceutically acceptable vehicle, carrier or excipient. Pharmaceutical compositions in accordance with the invention may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration. In the desired composition, the composition will contain an effective amount of the lysozyme as described above so as to be useful in the methods as set forth herein. The compositions may additionally contain stabilizers or pharmaceutically acceptable preservatives, such as thimerosal (ethyl (2-mercaptobenzoate-S)mercury sodium salt) (Sigma Chemical Company, St. Louis, Mo.).

For topical administration, the composition may be formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

It is also possible to use the compositions of the invention to fight infections in medical equipment, devices and implants as well. Medical devices or polymeric biomaterials and implants that can be coated with the compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the lysozyme or compositions containing it, or any pharmaceutical composition derived therefrom, to a surface of the device, preferably an outer surface that would be exposed to streptococcal bacterial infection. The surface of the device need not be entirely covered by the protein or composition to obtain the desired result of antibacterial activity. In the preferred method of the invention, the proteins and compositions of the invention will be most useful in killing bacteria that have 6-O acetylated peptidoglycans such as N,6-O-diacetylmuramic acid in their cell walls. The bacteria that can be killed by the proteins of the present invention will include such particularly resistant types as MRSA and VISA, and will also include bacteria such as streptococci, tuberculosis and anthrax.

In addition, the present invention provides isolated and/or purified nucleic acids which encode the protein and sequences as described above including SEQ ID NO:1. Such nucleic acids will be particularly useful in recombinantly preparing the proteins of the present invention. The preparation of recombinant proteins in accordance with the invention can be carried out using any means conventional used for such processes, and generally involve the transfection of the nucleic acid into a suitable vector, e.g., *E. coli*, yeast, bacteriophage, etc., and the culturing of the vector under conditions that will allow for the expression of the protein of the invention. The recombinant proteins are then isolated from the culture and/or purified for use in the applications described herein.

Still further, it is possible to obtain isolated antibodies in accordance with the invention. In this aspect of the present invention, isolated and/or purified antibodies are provided which can bind to the protein of the invention having SEQ ID NO:1 as set forth above. These antibodies may take the form of monoclonal or polyclonal antibodies, and these antibodies can be useful in situations wherein it is desired to bind the proteins of the invention. The monoclonal antibodies of the invention may be produced using conventional means, e.g., the method of Kohler and Milstein, Nature 256:495-497 (1975), and the polyclonal antibodies may be produced conventionally as well, e.g., by injection of an immunogenic amount of the protein of the invention into a suitable animal host, allowing sufficient time for the development of antibodies, and then recovering, isolating and/or purifying the antibodies obtained from the animal host. By immunogenic amount is meant that amount of the protein of the present invention which will obtain an immunogenic reaction in the host thus that the host generates antibodies to the injected protein.

The antibodies of the invention may thus be used in the detection of the presence of lysozyme under circumstances wherein its detection is desirable. In accordance with the invention, a preferred method of detecting the presence of lysozyme would involve the steps of obtaining a sample suspected of having lysozyme, e.g., a blood or tissue sample of a patient, introducing the antibody, and determining if there is any binding between the antibody and the sample. Such diagnostic assays can be formed into a kit which can contain the antibody, a sample container, means for introducing the antibody to the sample, and/or means to detect the binding of the antibody to the lysozyme in the sample. Such kits may utilize conventional labels or other means to detect binding.

Similarly, a kit in accordance with the invention may also be constructed to detect antibodies to lysozyme-Ch in a sample from a human or animal patient. In such a kit, a suitable amount of the proteins of the present invention as described above can be included in a kit along with means for introducing the patient sample to the protein, combined with means of detecting whether antibodies in the sample have bound to the protein in the kit. Such detection means may include suitable labels and will also allow for the quantification of the antibody titer in the patient.

In accordance with the present invention, methods are thus provided for preventing or treating infectious conditions, e.g., tuberculosis, which comprise administering an effective amount of the protein of the present invention to a human or animal patient in need of such treatment. Such treatment can be carried out using the methods disclosed above (i.e., topical, oral, injectable, etc.), and once again, an effective amount in this context refers to that non-toxic amount that will be administered to treat or prevent infection in the human or animal patient in need of such treatment. The effective amount will vary based on the nature of the patient and the severity of the particular infectious condition being treated.

The proteins of the present invention will thus be very useful in a variety of contexts, most particularly in the area of killing bacteria in a variety of settings

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

*Chalaropsis* Lysozyme Having the Correct Sequence for Use as Anti-bacterial Agent Overview:

Antibiotic-resistant bacteria are becoming an increasing issue in U.S. hospitals and communities. These pathogens complicate the treatment of serious infections and have been linked to extended hospitalizations, higher medical costs and high mortality rates. Lysozyme Ch, having both β-1,4-N-acetyl- and β-1,4-N,6-O-diacetylmuramidase activities, is an excellent candidate to develop into a new generation of antibiotics.

The present invention utilize the Lysozyme from fungus *Chalaropsis* species (Lysozyme Ch) as an antibiotic agent against many gram-positive bacteria, in particular *Staphylococcus aureus*. The present invention utilizes the hydrolytic activity of a Lysozyme from *Chalaropsis* Species (Lysozyme Ch) as a antibiotic agent against *Staphylococcus aureus* (*S. aureus*) and other gram-positive bacteria. In particular, the present invention utilizes the corrected sequence of Lysozyme Ch as indicated in SEQ ID NO:1. Lysozyme Ch is an extracellular hydrolase secreted by *Chalaropsis* fungus. It possesses both β-1,4-N-acetyl- and β-1,4-N,6-O-diacetylmuramidase activities and therefore is able to cleave 6-O-acetylated peptidoglycans such as that present in the cell walls of *S. aureus*.

The immediate applications for this antibiotic agent will include but not limited to use as topical antibiotic creams, which can be used to eradicate *S. aureus* nasal colonization and skin infections; veterinary therapeutics, which can be used to treat infections of *S. aureus* in animals; and human oral and injectable antibiotics.

In addition, the present inventors have now successfully determined the 3-D structure of the enzyme Lysozyme Ch, and the atomic coordinates for this structure are provided in Appendix A.

Experiments to Determine Activity of the Lysozyme Ch of the Present Invention:

To fully explore the anti-bacterial potential of Lysozyme Ch, a PEGylated Lysozyme Ch was tested for activity against Methicillin resistant staphylococcal cells, as well as other gram-positive or gram-negative pathogens, including Anthrax, Tuberculosis, and others; DNA of this enzyme was cloned into a suitable host to produce recombinant protein and enable specific mutagenesis.

Reducing Immunogenicity

PEGylation has been shown to reduce immunogenicity and increase half-life for a number of enzymes and antibodies for injection into human body. However, PEGylation can interfere with the enzymatic activities possibly due to attachment of PEG to active site groups. In the present case, it has been observed that certain PEG-attached lysozymes actually increase activity.

In one example, the *Chalaropsis* Lysozyme PEGylation was carried out using the steps as follows: (1) 15 mg of *Chalaropsis* Lysozyme and 1.05 g of Methoxypolyethylene glycol succinimidyl succinate (MPSS) was added into 0.1 M Sodium phosphate buffer to make final volume of 10 ml. (2)

Figure 1:
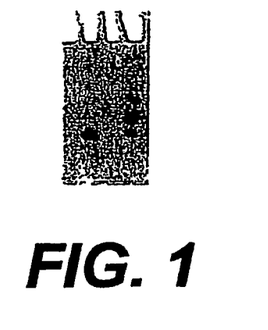
FIG. 1 is an SDS-Page of a PEGlylated lysozyme Ch in accordance with the invention.
Figure 2:
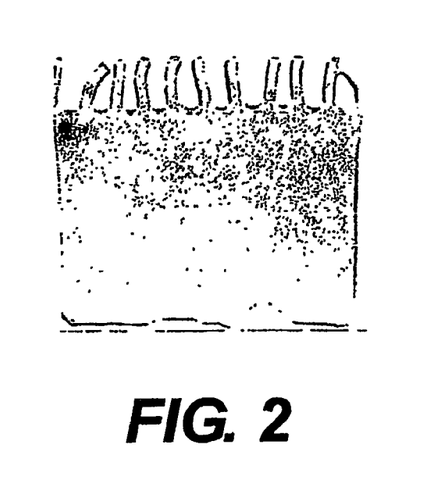
FIGS. 2 and 3 are two gel fractions of the PEGlylated lysozyme Ch in accordance with the invention.
Figure 3:
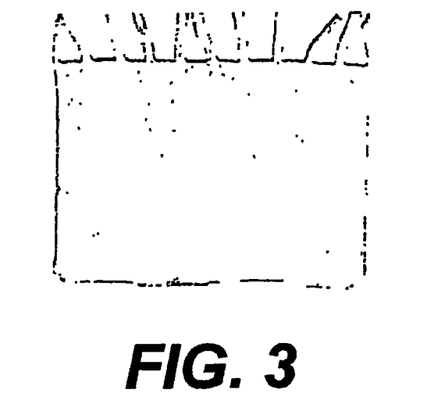

The mixture was allowed to shake on a rotator for 120 hours. The mixture was run on a SDS-PAGE to verify PEGylation (FIG. 1). (3) The mixture was concentrated with a YM-10 centriprep to a final volume of 1 ml. (4) The protein was loaded onto a XK16 column packed with Sephacryl S-300 resin. Fractions were collected every 2 min, i.e. 2 mls. (5) The following fractions are run on two gels (FIG. 2 and FIG. 3):

Gel1: MW, 28, 30, 35, 40, 45, 50, 55, 60, 65
Gel2: MW, 70, 75, 80, 83, 85, 90, 95, 99, 105.

Figure 4:
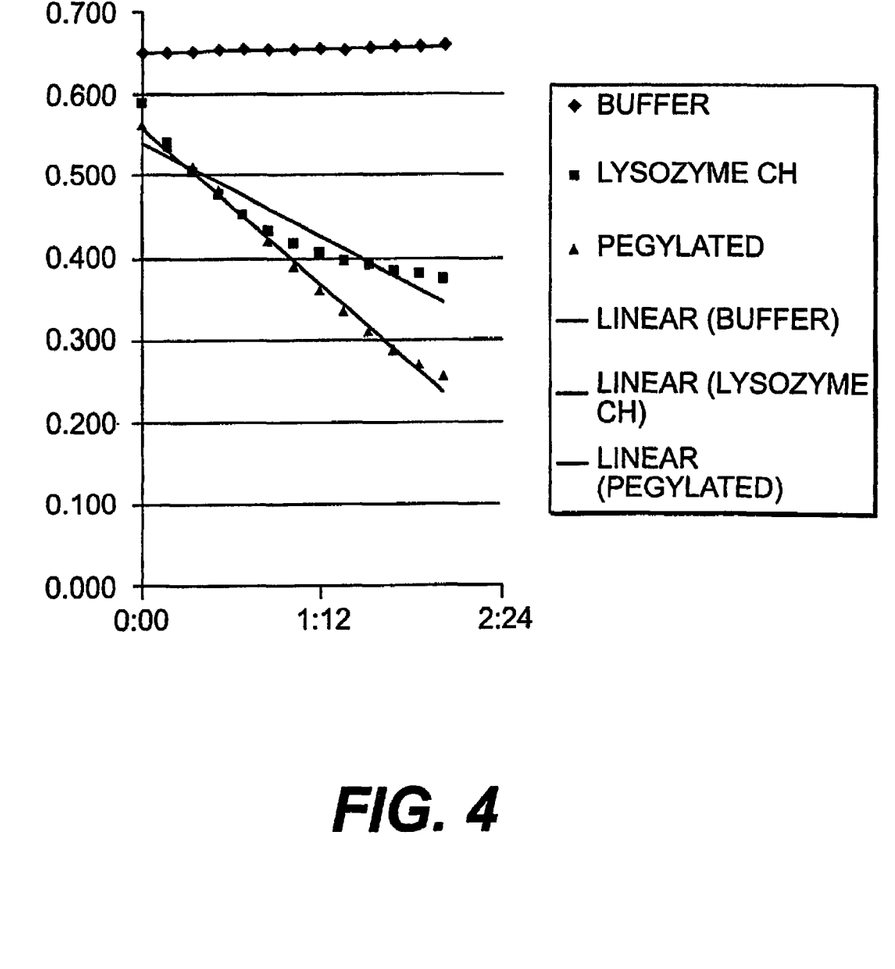
FIG. 4 shows the activity for the PEGylated protein in accordance with the invention.

(6) Based on the gel, it was decided that fractions around tube 55 was fully PEGylated, and thus fractions 53 to 57 were pooled and concentrated. (7) Activity was tested at 1 mg/ml for both native and PEGylated protein. As set forth in FIG. 4, the activity for the PEGylated protein was actually higher than that of the native non-PEGylated protein.

PEGylation of Lysozyme Ch

PEG with molecular weight of 5000 Dalton was chosen as a model system for PEGylation. Methoxypolyethylene glycol succinimidyl succinate (MPSS) was purchased from Sigma-Aldrich. MPSS uses activated succinimidyl groups to react with amino groups on the protein.

HEW Lysozyme was also PEGylated as a control experiment. Typically, 1 mg of Lysozyme dissolved in 0.1M phosphate buffer was mixed with 70 mg of MPSS (30:1 MPSS to protein molar ratio) and gently shaken at room temperature for 48 hours. The reactions were carried out with or without inhibitors. N-acetyl-Glucosamine and N,N',N''-triacetylchitotriose were used as inhibitors of HEW Lysozyme, Glucosamine hydrochloride and chitosan oligosaccharides were used as inhibitors of Lysozyme Ch. After verifying the degree of PEGylation with SDS PAGE, the solutions were buffer-exchanged for activity measurements.

Figure 5:
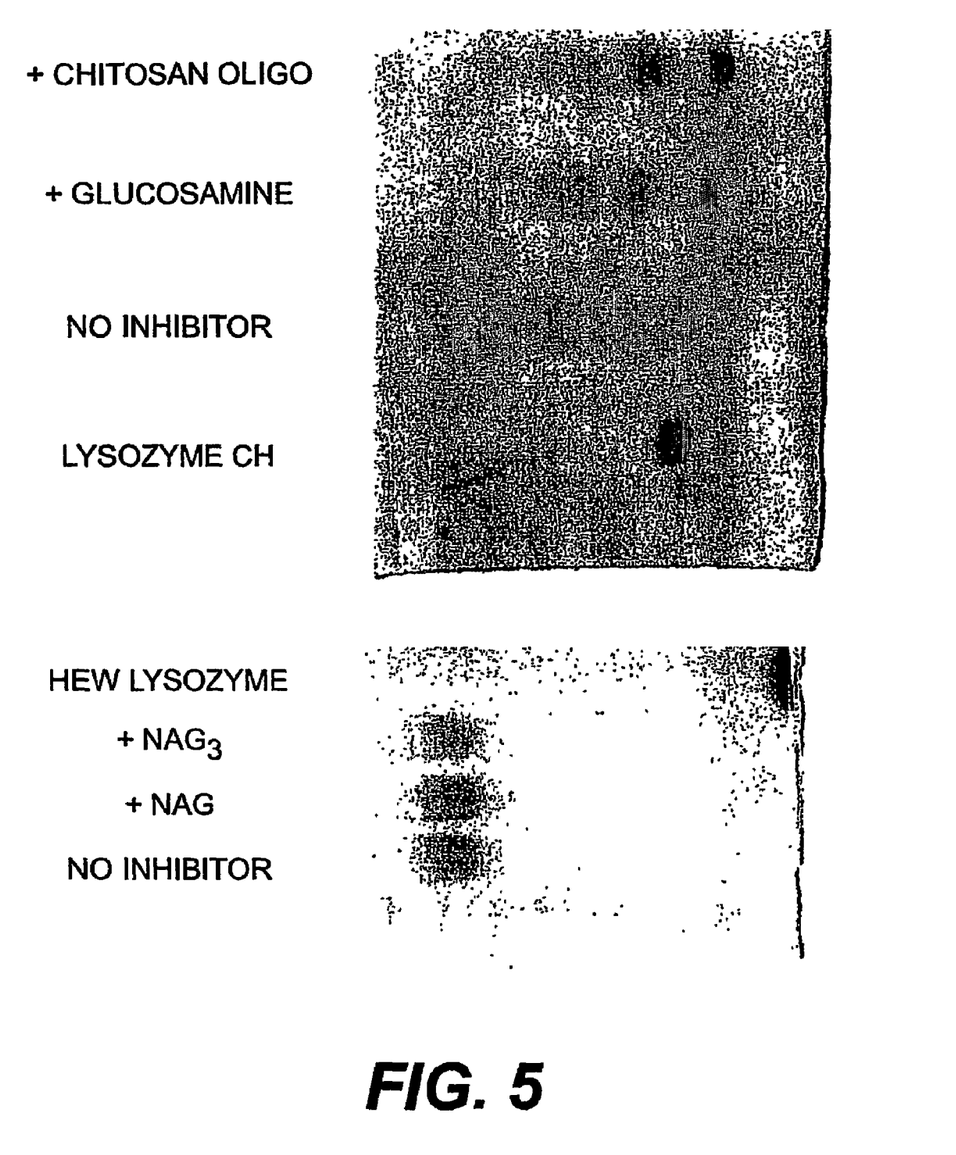
FIG. 5 is another SDS-Page of a PEGlylated lysozyme Ch in accordance with the invention.

SDS PAGE had shown that both enzymes are PEGylated. HEW Lysozyme is modified more completely than Lysozyme Ch (FIG. 5).

Capillary electrophoresis of the native and the modified enzymes subsequently confirmed the data from SDS PAGE (data not shown). Lysozyme Ch showed two forms of PEGylation and small amount of native protein left which was estimated to be less than 10%, indicating that higher ratio may be needed to fully PEGylate the enzyme.

Activity of the Enzymes after PEGylation.

HEW Lysozyme activity was tested with Micrococcus lysodeikticus cells in 50 mM Potassium Phosphate Buffer, pH 6.24 at 25° C. Absorbance at 450 nm is monitored for the turbidimetric rate determination on an Ultrospec 2000 spectrophotometer (ref).

Figure 6A:
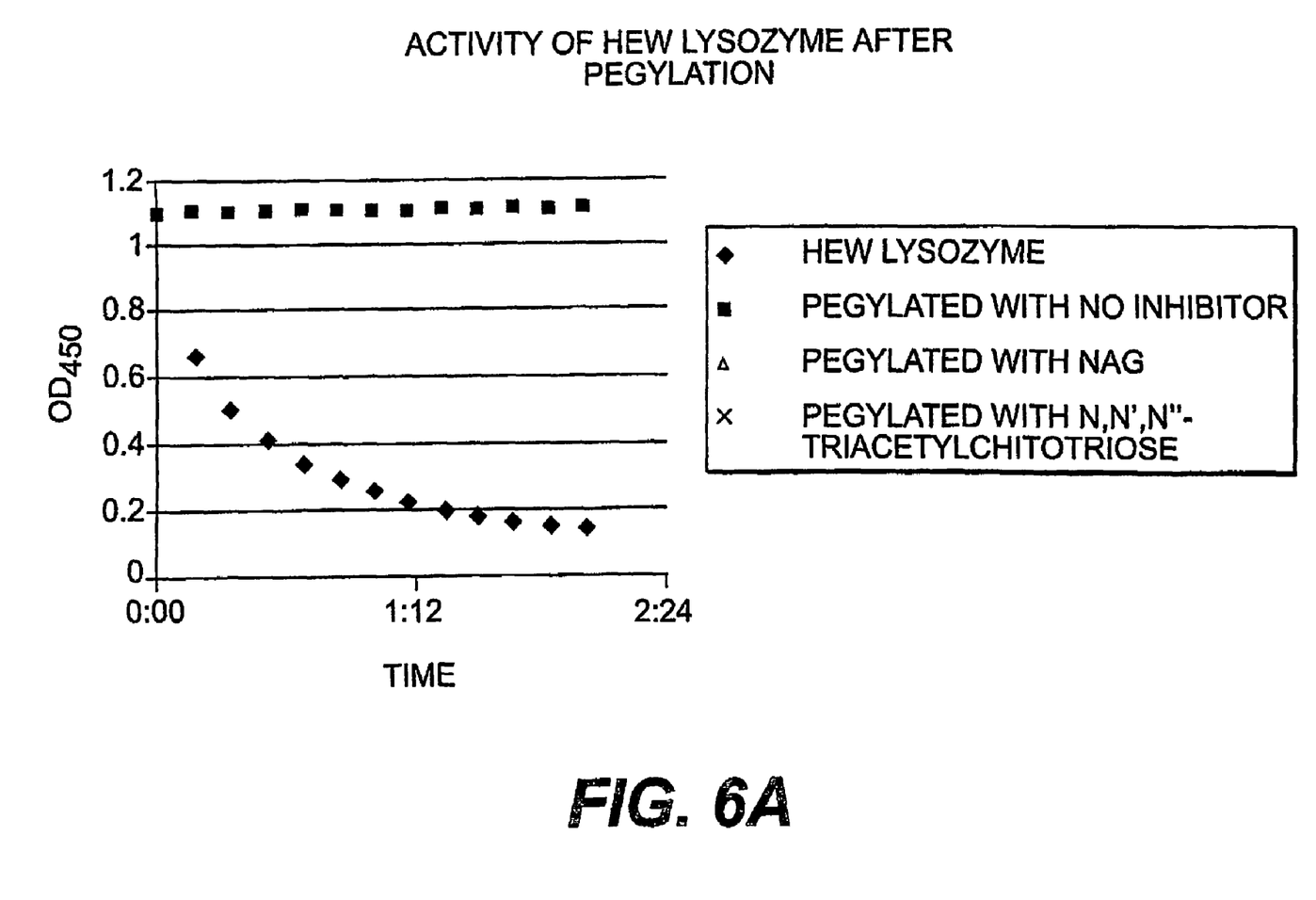
FIGS. 6A and 6B show the activity for PEGylated lysozymes in accordance with the invention.
Figure 6B:
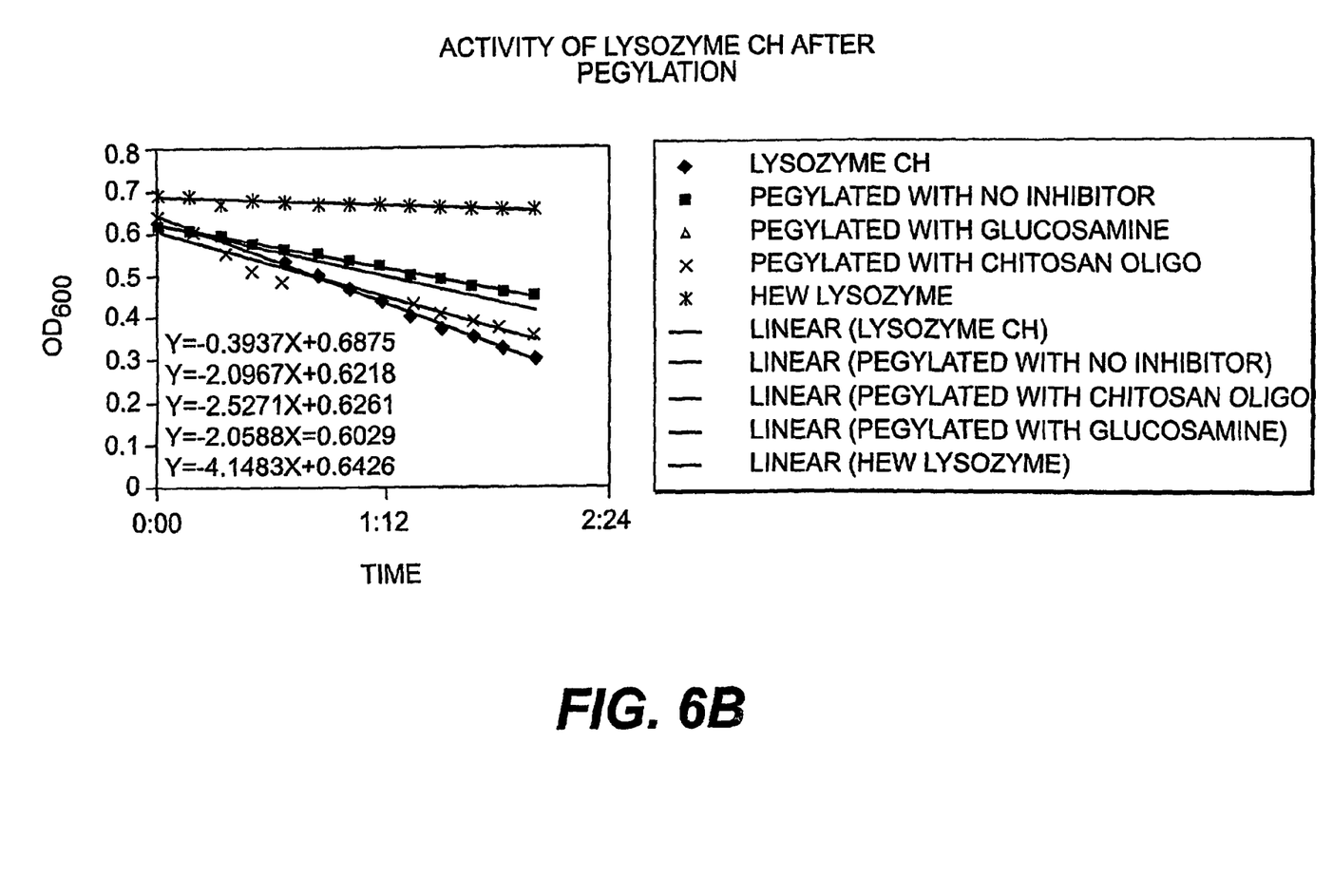

The native HEW Lysozyme reduces the absorbance in a non-linear way. After PEGylation, HEW Lysozyme obviously has lost its entire activity (FIG. 6) despite the presence of inhibitors.

Lysozyme Ch activity was measured with *Staphylococcus* cell wall in 50 mM Sodium acetate Buffer, pH 4.8 at 25° C. Absorbance at 600 nm is monitored for the turbidimetric rate determination on an Ultrospec 2000 spectrophotometer (Ref. 2).

As expected, Lysozyme Ch showed excellent activity against *Staphylococcus* cell wall while HEW Lysozyme has no activity. To our surprise, Lysozyme Ch retained considerable amount of the activity after PEGylation even in the absence of any inhibitor. The PEGylated enzyme in the presence of inhibitors showed higher remaining activity This phenomenon could possibly stem from remaining intact enzyme.

Activity Against Gram-Positive Pathogens

PEGylated Lysozyme Ch (pCH) can be produced with different ratio between the MPSS and the protein and different incubation time to generate homogenous degree of PEG attachment. Different degree of PEGylation can be selected at this time for further activity studies and immunogenic reactions. Final versions of the PEGylated proteins can be separated on gel filtration columns taking advantages of size difference.

Prior to PEGylating, it is also possible to use a reversible inhibitor which will block the access of PEG to the active site. Chitosan oligosaccharides are known to inhibit Lysozyme Ch. Oligosaccharides with different chain lengths will be isolated to test the inhibition. These inhibitors may also be critical in the determination of a complex structure and catalytic mechanism of the enzyme.

Purification of Inhibitors

Chitosan oligosaccharides have been known to be excellent inhibitors of this enzyme (Ref). Ideal inhibitor was shown to be with a chain length of 4 to 7, having the inhibition constant of $10^{-4}$ M.

Chitosan oligosaccharides with chain lengths less than 15 such as those available from Sigma-Aldrich can be used in the invention. CM sepharose was selected as a cation exchange resin. Using the right buffer and salt gradient, the sugars were well separated (data not shown). Each fractions were spotted on a filter paper and identified with ninhydrin. The fractions were freeze-dried and redissolved in water. Mass Spectroscopy was performed on the first peak. The molecular weight of the oligosaccharide was determined to be 1287.3 Dalton. This molecular weight indicates a chain length of 7.

Other procedures for making Chitosan oligosaccharides and purifying them have been previously published as would be recognized by one skilled in the art.

High Resolution X-ray Structure

Figure 7:
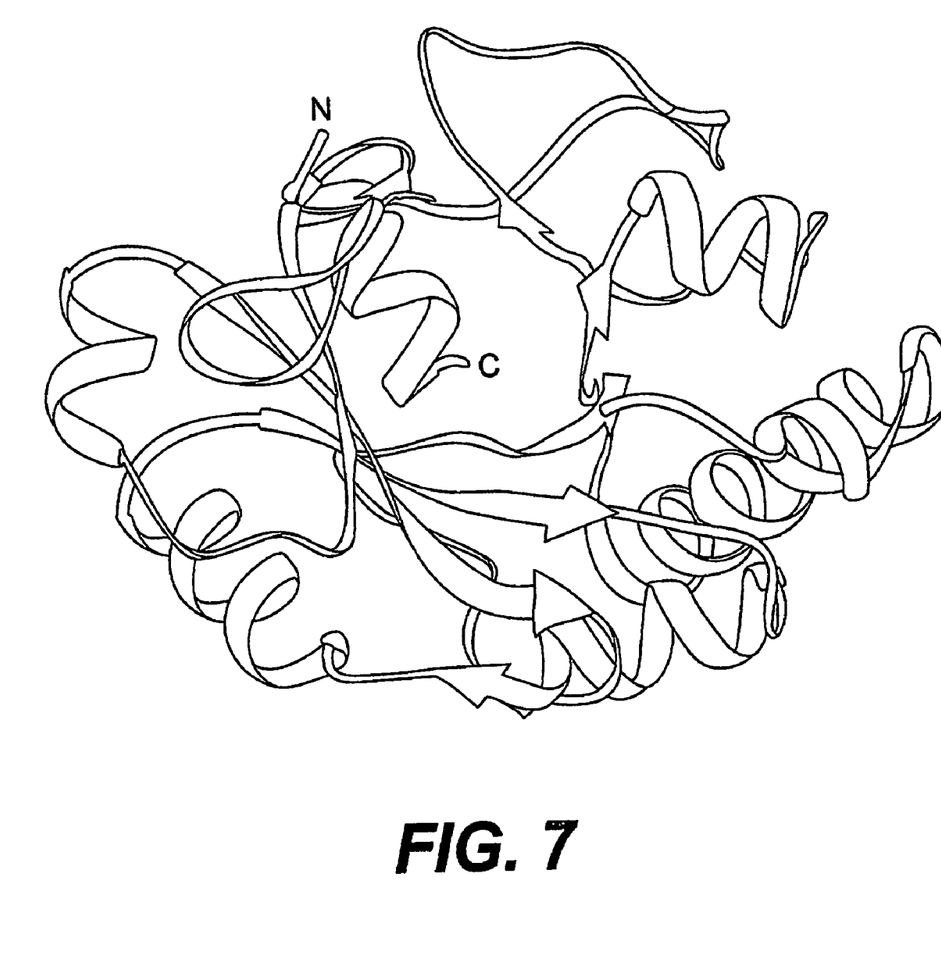
FIG. 7 shows the 3-dimensional structure of lysozyme Ch in accordance with the invention.

Crystals of Lysozyme Ch take more than a year to grow to a suitable size for x-ray. We have collected diffraction data up to 1.2 Å resolution. The protein forms an α-β-barrel structure as seen in FIG. 7. Because of the high resolution of the structures, we are able to identify several errors in the original sequence determined around 30 years ago. The structurally determined sequence of Lysozyme Ch is derived directly from experimental electron density. Comparisons with the same family sequences are also taken into consideration. See FIG. 8. The atomic coordinates of Lysozyme Ch are provided in Appendix A. In the corrected sequence of the invention, the number of amino acids has decreased from 211 to 207. There are sequence corrections throughout the entire molecule. To simplify, the sequence numbering are based on the original sequence in the following explanations.

Figure 8:
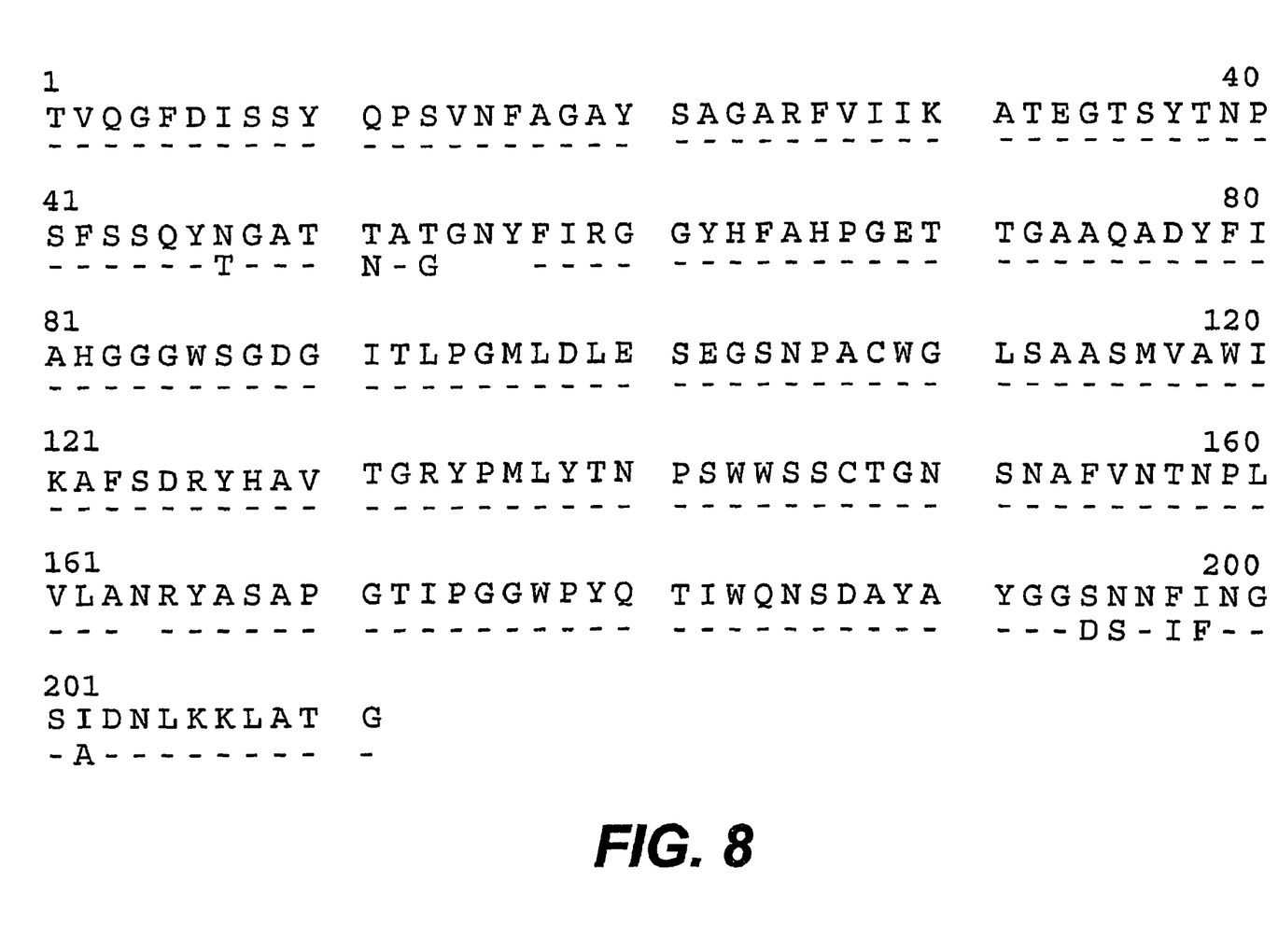
FIG. 8. shows the sequence of lysozyme Ch in accordance with the invention (SEQ ID NO:1) in comparison to the sequence as previously determined (SEQ ID NO:2).

The most important difference of appears to be Asp 194 (Ser). Asp 6 has been implicated to be involved in the catalytic activity. However, due to lack of an acidic or neutral hydrogen bonding partner, its role can not be confirmed definitively. This sequence change from Ser 194 to Asp puts an acidic amino acid right next to the Asp 6, forming the basis of the functional mechanism.

The three amino acids from 54 to 56 are not present and the experimental electron density indicated a GLY at position 53, sequence comparison also confirms it. Interestingly, although the ASN 164 is somewhat conserved in the family, the electron density clearly showed the deletion of this residue. The PHE 197 and ILE 198 are shown to be swapped.

The central hole consists three pairs of acidic residues interacting with each other, Asp 6 and Asp 194, Glu 36 and Glu 102, Asp 98 and Glu 100. The highly negative electrostatic potential makes it likely to be the substrate-binding site and the catalytic site. However, how the substrate is initially bound, which pair is carrying out the cleavage, and how the products are released are still not very clear. Structures of the protein complexed with enzymatic inhibitors would provide insightful information.

Subcloning DNA into a Suitable Host

To produce recombinant enzyme and enable the possible modifications to enhance the specific activity and efficiency of PEGylation, DNA of this enzyme can be subcloned into a bacterium such as *E. Coli*, a yeast such as *Pichia Pastoris*, or a virus such as *Baculo* Virus. In such methods, the DNA of the enzyme may be screened out using the cDNA library of fungus *Chalaropsis* Species.

Literature Cited—Incorporated by Reference

Shugar, D. (1952) *Biochimica et Biophysica Acta* 8, 302-309.
Hash, John (1967) *J. Bacteriology* 93(3), 1201-1202.

Other disclosures of patents related in general to atomic coordinates are set forth below and are incorporated herein by reference.

| | | |
|---|---|---|
| U.S. Pat. No.-5,322,933 | Jun. 21, 1994 | DAVIES et al. |
| U.S. Pat. No.-5,882,878 | Mar. 16, 1999 | SACCHETTINI |
| U.S. Pat. No.-5,939,528 | Aug. 17, 1999 | CLARDY et al. |
| U.S. Pat. No.-6,057,119 | May 02, 2000 | WILSON et at. |
| U.S. Pat. No.-6,093,573 | Jul, 25, 2000 | BEAMER et al. |
| U.S. Pat. No.-6,162,613 | Dec. 19, 2000 | SU et al. |
| U.S. Pat. No.-6,387,641 | May 14, 2002 | BELLON et al. |
| U.S. Pat. No.-6,459,996 | Oct. 01, 2002 | SOMERS et al. |
| US-20040082052A1 | Apr. 29, 2004 | |

| | | |
|---|---|---|
| US-20040009568A1 | Jan. 15, 2004 | |
| US-20040005686A1 | Jan. 08, 2004 | |
| US-20030229453A1 | Dec. 04, 2003 | |
| US-20030229453A1 | Dec. 11, 2003 | |
| US-20030224500A1 | Dec. 04, 2003 | |
| US-20030224368A1 | Dec. 04, 2003 | |
| US-20030224006A1 | Dec. 04, 2003 | |
| US-20030198997A1 | Oct. 23, 2003 | |
| US-20030187220A1 | Oct. 02, 2003 | |
| US-20030171904A1 | Sep. 11, 2003 | |
| US-20030171549A1 | Sep. 11, 2003 | |
| US-20030170868A1 | Sep. 11, 2003 | |
| US-20030166843A1 | Sep. 04, 2003 | |
| US-20030166233A1 | Sep. 04, 2003 | |
| US-20030165984A1 | Sep. 04, 2003 | |
| US-20030158384A1 | Aug. 21, 2003 | |
| US-20030143714A1 | Jul. 31, 2003 | |
| US-20030129656A1 | Jul. 10, 2003 | PARK et al. |
| US-20030125332A1 | Jul. 03, 2003 | |
| US-20030105010A1 | Jun. 05, 2003 | |
| US-20030101005A1 | May 29, 2003 | |
| US-20030096363A1 | May 22, 2003 | |
| US-20030082769A1 | May 01, 2003 | |
| US-20030073134A1 | Apr. 17, 2003 | |
| US-20030032779A1 | Jan. 13, 2003 | |
| US-20030018166A1 | Jan. 23, 2003 | |
| US-20020172670A1 | Nov. 21, 2002 | |
| US-20020165155A1 | Nov. 07, 2002 | |
| US-20020156585A1 | Oct. 24, 2002 | |
| US-20020132319A1 | Sep. 19, 2002 | |
| US-20020072105A1 | Jun. 13, 2002 | BENSON et al. |
| US-20020034802A1 | Mar, 21, 2002 | |
| US-20020031782A1 | | |
| US-20030032649A1 | Feb. 13, 2003 | GOLDSMITH et al. |

What is claimed is:

1. An isolated nucleic acid encoding a protein having the amino acid sequence as set forth in SEQ ID NO:1.

2. A method of preparing a protein having the amino acid sequence as set forth in SEQ ID NO:1 comprising transforming a vector comprising the nucleic acid encoding the amino acid sequence of SEQ ID NO:1 into an isolated host cell and culturing the host cell in a suitable medium for expressing and isolating said protein.

* * * * *

UNITED STATES PATENT AND TRADEMARK OFFICE
CERTIFICATE OF CORRECTION

PATENT NO.       : 7,662,607 B2                                           Page 1 of 1
APPLICATION NO. : 10/566243
DATED            : February 16, 2010
INVENTOR(S)      : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this

Thirtieth Day of November, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 207
<212> TYPE: PRT
<213> ORGANISM: Chalaropsis sp.

<400> SEQUENCE: 1

Thr Val Gln Gly Phe Asp Ile Ser Ser Tyr Gln Pro Ser Val Asn Phe
1               5                   10                  15

Ala Gly Ala Tyr Ser Ala Gly Ala Arg Phe Val Ile Ile Lys Ala Thr
                20                  25                  30

Glu Gly Thr Ser Tyr Thr Asn Pro Ser Phe Ser Ser Gln Tyr Thr Gly
            35                  40                  45

Ala Thr Asn Ala Gly Phe Ile Arg Gly Gly Tyr His Phe Ala His Pro
        50                  55                  60

Gly Glu Thr Thr Gly Ala Ala Gln Ala Asp Tyr Phe Ile Ala His Gly
65                  70                  75                  80

Gly Gly Trp Ser Gly Asp Gly Ile Thr Leu Pro Gly Met Leu Asp Leu
                85                  90                  95

Glu Ser Glu Gly Ser Asn Pro Ala Cys Trp Gly Leu Ser Ala Ala Ser
            100                 105                 110

Met Val Ala Trp Ile Lys Ala Phe Ser Asp Arg Tyr His Ala Val Thr
        115                 120                 125

Gly Arg Tyr Pro Met Leu Tyr Thr Asn Pro Ser Trp Trp Ser Ser Cys

```
               130                 135                 140
Thr Gly Asn Ser Asn Ala Phe Val Asn Thr Asn Pro Leu Val Leu Ala
145                 150                 155                 160

Arg Tyr Ala Ser Ala Pro Gly Thr Ile Pro Gly Gly Trp Pro Tyr Gln
                165                 170                 175

Thr Ile Trp Gln Asn Ser Asp Ala Tyr Ala Tyr Gly Gly Asp Ser Asn
                180                 185                 190

Ile Phe Asn Gly Ser Ala Asp Asn Leu Lys Lys Leu Ala Thr Gly
                195                 200                 205

<210> SEQ ID NO 2
<211> LENGTH: 211
<212> TYPE: PRT
<213> ORGANISM: Chalaropsis sp.

<400> SEQUENCE: 2

Thr Val Gln Gly Phe Asp Ile Ser Ser Tyr Gln Pro Ser Val Asn Phe
1               5                   10                  15

Ala Gly Ala Tyr Ser Ala Gly Ala Arg Phe Val Ile Ile Lys Ala Thr
                20                  25                  30

Glu Gly Thr Ser Tyr Thr Asn Pro Ser Phe Ser Ser Gln Tyr Asn Gly
                35                  40                  45

Ala Thr Thr Ala Thr Gly Asn Tyr Phe Ile Arg Gly Tyr His Phe
50                  55                  60

Ala His Pro Gly Glu Thr Thr Gly Ala Ala Gln Ala Asp Tyr Phe Ile
65                  70                  75                  80

Ala His Gly Gly Gly Trp Ser Gly Asp Gly Ile Thr Leu Pro Gly Met
                85                  90                  95

Leu Asp Leu Glu Ser Glu Gly Ser Asn Pro Ala Cys Trp Gly Leu Ser
                100                 105                 110

Ala Ala Ser Met Val Ala Trp Ile Lys Ala Phe Ser Asp Arg Tyr His
                115                 120                 125

Ala Val Thr Gly Arg Tyr Pro Met Leu Tyr Thr Asn Pro Ser Trp Trp
                130                 135                 140

Ser Ser Cys Thr Gly Asn Ser Asn Ala Phe Val Asn Thr Asn Pro Leu
145                 150                 155                 160

Val Leu Ala Asn Arg Tyr Ala Ser Ala Pro Gly Thr Ile Pro Gly Gly
                165                 170                 175

Trp Pro Tyr Gln Thr Ile Trp Gln Asn Ser Asp Ala Tyr Ala Tyr Gly
                180                 185                 190

Gly Ser Asn Asn Phe Ile Asn Gly Ser Ile Asp Asn Leu Lys Lys Leu
                195                 200                 205

Ala Thr Gly
210
```